US006515172B2

(12) United States Patent
Grottenmüller et al.

(10) Patent No.: US 6,515,172 B2
(45) Date of Patent: Feb. 4, 2003

(54) PROCESS FOR THE PREPARATION OF PERFLUOROCARBOXYLIC ACIDS

(75) Inventors: Ralf Grottenmüller, Burghausen (DE); Wolfgang Knaup, Burgkirchen (DE); Anton Probst, Erlbach (DE); Klaus Dullinger, Burgkirchen (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 09/902,395

(22) Filed: Jul. 10, 2001

(65) Prior Publication Data

US 2002/0147357 A1 Oct. 10, 2002

(30) Foreign Application Priority Data

Jul. 10, 2000 (DE) .......................................... 100 33 255

(51) Int. Cl.[7] .............................................. C07C 51/215
(52) U.S. Cl. ...................... 562/520; 562/523; 562/524; 562/541; 562/542; 562/543; 562/544
(58) Field of Search ................................ 562/520, 542, 562/543, 544, 523, 524, 541

(56) References Cited

U.S. PATENT DOCUMENTS

| 4,138,417 A | 2/1979 | Ukihashi et al. |
| 4,221,734 A | 9/1980 | Commeyras et al. |
| 4,400,325 A | 8/1983 | Von Werner et al. |
| 4,692,493 A | 9/1987 | Sulzbach et al. |
| 4,751,027 A | 6/1988 | Von Werner et al. |
| 5,736,012 A | * 4/1998 | Thenappan et al. ......... 562/542 |
| 6,111,136 A | * 8/2000 | Marzouk et al. ............ 562/113 |

FOREIGN PATENT DOCUMENTS

| DE | 27 56 169 | 6/1978 |
| DE | 30 43 249 | 7/1982 |
| DE | 35 12 633 | 10/1986 |
| DE | 36 06 174 | 8/1987 |

OTHER PUBLICATIONS

Hue et al, Huaxue Xuebao, vol 48(9), 1990, English abstract only.*
English Translation of the Abstract of DE 30 43 249, 1982.
English Translation of the Abstract of DE 27 56 169, 1978.
English Translation of the Abstract of DE 35 12 633, 1986.
English Translation of the Abstract of DE 36 06 174, 1987.

* cited by examiner

Primary Examiner—Shailendra Kumar
(74) Attorney, Agent, or Firm—Scott E. Hanf

(57) ABSTRACT

Process for the preparation of perfluorocarboxylic acids of the formula $R_F$—COOH, salts thereof and esters thereof from perfluoroalkyl iodides of the formula $R_F'$—I, in which $R_F$ and $R_F'$ are cyclic, branched or linear, saturated or unsaturated perfluoroalkyl radicals, by activating the perfluoroalkyl iodides in the presence of oxygen and in organic solvents.

12 Claims, No Drawings

PROCESS FOR THE PREPARATION OF PERFLUOROCARBOXYLIC ACIDS

BACKGROUND OF THE INVENTION

The invention relates to a process for the preparation of perfluorocarboxylic acids of the formula $R_F$—COOH, salts thereof and esters thereof from perfluoroalkyl iodides of the formula $R_F'$—I by oxidation with oxygen under the action of light, metals, free-radical and $R_F'$ can be cyclic, branched or linear, saturated or unsaturated perfluoroalkyl radicals.

Perfluorocarboxylic acids are compounds with extremely high chemical and thermal stability and excellent surface-active properties. There is a great need for perfluorocarboxylic acids, sometimes in high purity, for a multitude of different applications. Their excellent emulsifier properties are utilized, for example, during the emulsion polymerization of fluorinated olefins, such as, for example, tetrafluoroethylene. For example, DE-A-3512633 describes the use of alkali metal and ammonium salts of perfluorooctanoic acid as emulsifier in the preparation of shear-stable PTFE copolymer dispersions.

A number of processes for the preparation of perfluorocarboxylic acids are already known, but they all have serious disadvantages.

For example, perfluorocarboxylic acids can be obtained by hydrolysis of perfluorocarboxylic acid halides, which are obtained from the corresponding fluorine-free The handling of liquid hydrogen fluoride, the yield which decreases considerably with increasing chain length and the formation of chain-branched rearrangement products limit the applicability of this process.

DE-A-3606174 describes the oxidation of perfluoroalkylethylene of the formula $F(CF_2)_n$—CH=CH$_2$ with permanganate to give perfluorocarboxylic acids. This process has the disadvantage that relatively large amounts of manganese oxides are produced as waste material. The ozone described in U.S. Pat. No. 4,138,417 as oxidizing agent for perfluoroalkylethylene is not practicable on an industrial scale either.

DE-A-2756169 describes the reaction of perfluoroalkyl iodide $F(CF_2)_n$—I with zinc or with activated zinc and carbon dioxide to give perfluorocarboxylic acids. The low yield, the need for certain solvents and the consumption of zinc are disadvantages of this process.

DE-A-3043249 describes the oxidation of perfluoroalkyl iodide $F(CF_2)_n$—I with fuming sulfuric acid at temperatures of 100–180° C. The difficult handling of fuming sulfuric acid and the high requirements placed on the chemical resistance of the apparatus present considerable difficulties when this process is carried out on an industrial scale.

SUMMARY OF THE INVENTION

We have now found a process which permits the preparation of perfluorocarboxylic acids in high purity from readily accessible perfluoroalkyl iodide under mild reaction conditions and with the avoidance of relatively large amounts of waste products. Surprisingly, it has been found that perfluoroalkyl iodides in organic solvent with the action of light or other activating substances or conditions in the presence of oxygen, with even atmospheric oxygen sufficing, can be converted to perfluorocarboxylic acids of high purity in high yields even at room temperature. Suitable perfluoroalkyl iodides are cyclic, branched or linear, saturated or unsaturated compounds. Examples of such compounds are $F(CF_2)_i$—I, $(CF_3)_2CF$—$(CF)_j$—I, $F(CF_2)_k$—CF$(CF_3)$—I, $F(CF_2)_l$—CF$(CF_3)$—CF$_2$—I, $F$—CF$_2$—CF$(CF_3))_m$—I and F—$(CF_2$—CF$_2)_n(CF_2$—CF$(CF_3))_p$—I, where i, j, k, l, m, n and p are each integers from 0 to 20. Preferred organic solvents are, in particular, lower alcohols such as methanol and ethanol. As well as light, suitable activators for perfluoroalkyl iodide are also relatively high temperatures, metal catalysis or free-radical sources, such as, for example, free-radical initiators.

DESCRIPTION OF THE PREFERRED EMBODIMENTS

The perfluoroalkyl iodide is dissolved in the organic solvent in a concentration of, preferably, 1–50% by weight. In principle, a very wide variety of organic solvents are possible. Those which have proven particularly suitable, however, are short-chain linear, branched or cyclic alcohols having $\leq 10$ carbon atoms, such as, for example, methanol, ethanol, propanol, butanol or isopropanol. The perfluoroalkyl iodide solution is gassed with oxygen. It even suffices to pass air through the solution, although pure oxygen increases the reaction rate. To further accelerate the reaction, an air or oxygen pressure above atmospheric can also be applied. The reaction can be started at room temperature by irradiation with light. It is known that the dissociation of perfluoroalkyl iodides into perfluoroalkyl radical and iodine radical can be triggered photochemically. Even normal daylight suffices for this purpose. Irradiation with UV light, e.g. using Hg lamps, is of course considerably more effective. The wavelength of the incident light should preferably be within the range of UV absorption of perfluoroalkyl iodides at about 250–310 nm. Instead of light, it is also possible to use free-radical sources, such as azo compounds, peroxides, percarbonates or other known free-radical initiators which produce free radicals thermally or as a result of a chemical reaction. The reaction would then have to be carried out at higher temperatures corresponding to the decomposition temperature of the free-radical initiator used. Light as a reaction trigger has the advantage over free-radical initiators that no undesired fragments are left behind, but can only be realized on an industrial scale at relatively great expense. Apart from light and free-radical initiators, another possible way of triggering the reaction is to use certain metals in homogeneous or heterogeneous form. It is known that perfluoroalkyl iodides can be activated by metals.

For example, the reaction in ethanol under the influence of light, metal catalysis or a free-radical source proceeds in accordance with the following empirical formula:

$$2F(CF_2)_n-CF_2-I+5\ CH_3CH_2-OH+O_2 \rightarrow 2F(CF_2)_n-CO-OCH_2CH_3+4HF+CH_3CH(OCH_2CH_3)_2+H_2O$$

If the solvent used is alcohol, from the perfluorocarbonyl fluoride, which is primarily formed during the reaction, directly arises the corresponding perfluorocarboxylic ester, and the alcohol is largely oxidized to give the aldehyde, which is condensed with excess alcohol to give the acetal. In some cases, continuing oxidation of the solvent, e.g. to the carboxylic acid, takes place.

For the work-up, if a water-miscible solvent is present, it is possible, following removal of the iodine, to dilute with water whereupon a lower phase separates out which consists of perfluorocarboxylic acid and esters thereof and any unreacted perfluoroalkyl iodide still present. The lower phase is separated off and purified by distillation. If the iodine has been removed beforehand by chemical means by reduction or oxidation or by physical methods, the reaction solution can be worked up directly by fractional distillation. The HF or fluoride formed during the reaction can be precipitated out as sparingly soluble $CaF_2$ by adding calcium salts, such as, for example $CaCl_2$, $CaCO_3$ or $Ca(OH)_2$ and filtered off.

Unless stated otherwise, the examples described in Tables 1 to 3 were carried out in accordance with the following general procedure.

Perfluorooctyl iodide ($C_8F_{17}I$, ®Fluowet I 800-CLARIANT) is dissolved in the solvent in the given weight ratio. The experiments involving exposure to a UV lamp were carried out in a water-cooled 250 ml exposure apparatus made of quartz glass. The experiments with initiators other than light were carried out in a darkened apparatus. The solution is gassed with air via a capillary. Stirring is carried out for the given time at the given temperature. Analysis is carried out from the reaction solution without further work-up by $^{19}$F-NMR.

gassing with air over the course of 76 hours forms 9% ethyl perfluorooctanoate (No. 1). If the experiment is carried out without oxygen under $N_2$ atmosphere (No. 2), without solvent (No. 3) or without the action of light or other initiators (No. 4), no reaction takes place. If UV light is used instead of daylight (No. 5), the reaction proceeds considerably more rapidly and in a higher yield. UV light and $N_2$ atmosphere (No. 6) lead to the formation of 1H-perfluorooctane. The reaction proceeds with a comparable rate and yield in the case of perfluoroalkyl iodides of different chain lengths or with chain sections (No. 5, 7, 8, 9

TABLE 1

| No. | | $R_FI$ | Solv: $R_FI$ g:g | Initiator | Time in h | Temp. in °C | Result $R_FI$ | $R_FH$ | $R'_FCOR$ | Other |
|---|---|---|---|---|---|---|---|---|---|---|
| 1 | Ethanol | $C_8F_{17}I$ | 150:15 | daylight | 76 | 25 | 87% | <1% | 13% | — |
| 2 | Ethanol | $C_8F_{17}I$ | 100:10 | daylight | 68 | 25 | >99% | <1% | <1% | under $N_2$ atmosphere |
| 3 | — | $C_8F_{17}I$ | 0:100 | daylight | 50 | 25 | >99% | <1% | <1% | — |
| 4 | Ethanol | $C_8F_{17}I$ | 150:15 | — | 70 | 25 | >99% | <1% | <1% | — |
| 5 | Ethanol | $C_8F_{17}I$ | 150:50 | UV lamp | 8 | 25 | 67% | <1% | 33% | — |
| 6 | Methanol | $C_8F_{17}I$ | 200:30 | UV lamp | 5 | 40 | 84% | 9% | <1% | under $N_2$ atmosphere |
| 7 | Methanol | $C_6F_{13}I$ | 150:50 | UV lamp | 8 | 25 | 61% | <1% | <39% | — |
| 8 | Methanol | $C_{10}F_{21}I$ | 150:50 | UV lamp | 8 | 25 | 64% | <1% | <36% | — |
| 9 | Methanol | $R_FI$-6* | 150:50 | UV lamp | 8 | 25 | 60% | <1% | <40% | — |
| 10 | Methanol | $R_FI$-8* | 150:50 | UV lamp | 8 | 25 | 68% | <1% | <32% | — |
| 11 | Methanol | i-$C_7F_{15}$** | 150:50 | UV lamp | 8 | 25 | 71% | <1% | <29% | — |

*$R_FI$-6: 44% $C_6F_{13}I$, 35% $C_8F_{17}I$, 15% $C_{10}F_{21}I$, 6% ≧ $C_{12}F_{25}I$

*$R_FI$-8: 14% $C_6F_{13}I$, 53% $C_8F_{17}I$, 21% $C_{10}F_{21}I$, 12% ≧ $C_{12}F_{25}I$

**i-$C_7F_{15}$: $(CF_3)_2CF(CF_2)_4$—I

Table 1 shows that perfluorooctyl iodide under the influence of daylight at room temperature (25° C.) and with and 10) and in the case of branched perfluoroalkyl iodides (No. 11).

TABLE 2

| No. | | $R_FI$ | Solv: $R_FI$ g:g | Initiator | Time in h | Temp. in °C | Result $R_FI$ | $R_FH$ | $R'_FCOR$ | Other |
|---|---|---|---|---|---|---|---|---|---|---|
| 1 | Ethanol | $C_8F_{17}I$ | 150:15 | UV lamp | 12 | 25 | 63% | <1% | 37% | — |
| 2 | Isopropanol | $C_8F_{17}I$ | 150:15 | UV lamp | 12 | 25 | 65% | <1% | 35% | — |
| 3 | Methanol | $C_8F_{17}I$ | 150:15 | UV lamp | 10 | 25 | 52% | <1% | 48% | — |
| 4 | Cyclohexane | $C_8F_{17}I$ | 150:15 | UV lamp | 10 | 25 | 93% | <1% | 7% | — |
| 5 | Acetonitrile | $C_8F_{17}I$ | 150:15 | UV lamp | 12 | 25 | 95% | <1% | 5% | — |
| 6 | Ethyl acetate | $C_8F_{17}I$ | 150:15 | UV lamp | 12 | 25 | 94% | <1% | 6% | — |
| 7 | Glycerol | $C_8F_{17}I$ | 150:15 | UV lamp | 8 | 25 | 92% | <1% | 8% | — |
| 8 | Cyclohexanol | $C_8F_{17}I$ | 150:15 | UV lamp | 8 | 25 | 79% | <1% | 21% | — |
| 9 | tert-Butanol | $C_8F_{17}I$ | 150:15 | UV lamp | 12 | 25 | 59% | <1% | 41% | — |

Table 2 shows the effect of different solvents. Alcohols such as methanol (No. 3), ethanol (No. 1), isopropanol (No. 2), tert-butanol (No. 9) and cyclohexanol (No. 8) produce high yields of the desired perfluorooctylcarbonyl compounds in a short time. In solvents which do not carry OH functions, such as cyclohexane (No. 4), acetonitrile (No. 5) and ethyl acetate (No. 6), the conversions are lower under comparable conditions.

glass with water cooling and Hg lamp at 25–30° C. Air is passed in via a capillary throughout the entire reaction time. After the solution has turned brown after stirring for 4 h at 25–30° C. as a result of liberated iodine, the reaction is interrupted, and the solution is poured into a 1 l beaker, where it is stirred with 40 g of iron powder until the color of the iodine has disappeared (about 15 min). After the precipitate and the excess iron powder have been filtered off,

TABLE 3

| | | Solv: $R_FI$ | | Time | Temp. | Result | | | |
|---|---|---|---|---|---|---|---|---|---|
| No. | | $R_FI$ | g:g | Initiator | in h | in ° C. | $R_FI$ | $R_FH$ | $R'_FCOR$ | Other |
| 1 | Methanol | $C_8F_{17}I$ | 150:15 | — | 24 | 25 | 98% | <1% | <1% | exclusion of light |
| 2 | Methanol | $C_8F_{17}I$ | 150:15 | daylight | 24 | 25 | 87% | <1% | 13% | — |
| 3 | Methanol | $C_8F_{17}I$ | 150:20 | UV lamp | 12 | 25 | 52% | <1% | 48% | — |
| 4 | Methanol | $C_8F_{17}I$ | 120:50 | VA 044*[1] (3 g) | 13 | 55 | 72% | <1% | 28% | exclusion of light |
| 5 | Methanol | $C_8F_{17}I$ | 200:60 | Perkadox 16S*[2] (3 g) | 8 | 45 | 51% | 2% | 47% | exclusion of light |
| 6 | Methanol | $C_8F_{17}I$ | 200:60 | Perkadox 16S*[2] (5 g) | 9 | 45 | 33% | 3% | 64% | exclusion of light |
| 7*[6] | Methanol | $C_8F_{17}I$ | 45:15 | Temp./DTBP*[3] | 12 | 150 | <1% | 68% | 32% | exclusion of light |
| 8*[6] | Methanol | $C_8F_{17}I$ | 45:15 | Temp. | 12 | 100 | 40% | 43% | 17% | exclusion of light |
| 9*[6] | Methanol | $C_8F_{17}I$ | 45:15 | Temp. | 12 | 150 | <1% | 90% | 10% | exclusion of light |
| 10*[6] | Methanol | $C_8F_{17}I$ | 45:15 | Temp. | 12 | 180 | <1% | >99% | <1% | exclusion of light |
| 11 | Methanol | $C_8F_{17}I$ | 150:50 | Zinc powder | 5 | 25 | 55% | 36% | 9% | exclusion of light |
| 12 | Methanol | $C_8F_{17}I$ | 100:15 | Fe powder | 2 | 50 | 94% | 1% | 5% | exclusion of light |
| 13 | Methanol | $C_8F_{17}I$ | 100:15 | Pd*[4] | 5 | 50 | 96% | <1% | 4% | exclusion of light |
| 14 | Methanol | $C_8F_{17}I$ | 250:50 | Cu powder | 6 | 50 | 38% | <1% | 62% | exclusion of light |
| 15*[6] | Methanol | $C_8F_{17}I$ | 45:15 | Temp./Cu powder | 12 | 180 | <1% | 39% | 71% | exclusion of light |
| 16 | Methanol | $C_8F_{17}I$ | 70:15 | Cu—/Fe powder | 5 | 50 | 66% | <1% | 34% | exclusion of light |
| 17*[6] | Methanol | $C_8F_{17}I$ | 60:15 | Pd*[4] | 12 | 120 | 3% | 77% | 20% | exclusion of light |
| 18*[6] | Methanol | $C_8F_{17}I$ | 60:15 | Ru*[5] | 12 | 120 | 7% | 74% | 19% | exclusion of light |

*[1]Cationic azo free-radical initiator
*[2]Peroxy dicarbonate free-radical initiator
*[3]Di-tert-butyl peroxide
*[4]Type E 106 R/W, Degussa
*[5]Type H 105 RA, Degussa
*[6]The experiments at temperatures greater than 60° C. were carried out in a 250 ml steel autoclave with an air atmosphere.

Table 3 shows the effect of different substances or conditions which activate perfluoroalkyl iodide.

Under otherwise comparable conditions, a higher light intensity leads to a more rapid reaction (No. 1, 2 and 3). Instead of light, it is also possible to use free-radical initiators customarily employed for free-radical reactions (No. 4, 5, 6 and 7). The conversion of $R_FI$ depends here on the amount of initiator used (No. 5 and 6). In the case of free-radical initiators which only produce free radicals at relatively high temperatures, such as, for example, di-tert-butyl peroxide at 150° C., relatively large amounts of $R_FH$ are formed (No. 7). Temperatures above 70° C. without other catalytically effective conditions likewise produce perfluorooctylcarbonyl compounds, but particularly from 100° C. upwards, a preferred formation of $R_FH$ is to be observed (No. 8, 9 and 10). Metals such as, for example, copper are catalytically active even at room temperature (No. 14). Base metals such as zinc and iron produce low conversions (No. 12) or preferably $R_FH$ (No. 11). Metals such as palladium (No. 17) and ruthenium (No. 18) produce product mixtures of perfluorooctylcarbonyl compounds and $R_FH$ at relatively high temperatures.

EXAMPLES

The two examples below describe ways of achieving complete conversion of pefluorooctyl iodide to methyl perfluorooctanoate.

Example 1
Catalysis with UV Light 75 g of perfluorooctyl iodide and 300 ml of methanol are introduced into a 500 exposure apparatus made of quartz the now clear solution is returned to the exposure apparatus and the photochemical reaction is continued. The purification step has to be carried out another 3 times, in each case after 5 h, during the course of the reaction. Following complete conversion (check using $^{19}$F-NMR), the solution is washed 5 times with water, and the fluorine-containing lower phase is subjected to fractional distillation. Yield: 53.9 g (92%) of methyl perfluorooctanoate as colorless liquid, boiling point 158–161° C.

Example 2
Metal Catalysis with Copper 75 g of perfluorooctyl iodide and 300 ml of ethanol are stirred together with 20 g of copper powder at 50° C. for 12 h in a heatable 500 ml three-necked flask fitted with a stirrer. Then, at intervals of 6 h, 1.5 g of fresh copper powder in each case are added 8 times. After complete conversion (check using $^{19}$F-NMR), the mixture is filtered off and the filtrate is washed a number of times with water. The residue is thoroughly extracted using sulfuric acid. The sulfuric acid solution is concentrated by evaporation and the perfluorooctanoic acid present is converted into the ethyl ester by adding an excess of ethanol. The combined fluorine phases are subjected to fractional distillation. Yield: 52.7 g (87%) of ethyl perfluorooctanoate as colorless liquid, boiling point 180–184° C.

What is claimed is:
1. A process for the preparation of perfluorocarboxylic acids of the formula $R_F$—COOH, salts thereof and esters thereof from perfluoroalkyl iodides of the formula $R_F'$—I, in which $R_F$ and $R_F'$ are cyclic, branched or linear, saturated or unsaturated perfluoroalkyl radicals, by activating the per- fluoroalkyl iodides in the presence of an activating agent, oxygen and in organic solvents, wherein said activating agent is selected from the group consisting of: free-radical sources; metals in heterogeneous or homogeneous form; temperature; and combinations thereof.

2. The process as claimed in claim 1, wherein the activation of the perfluoroalkyl iodides is performed in the absence of light.

3. The process as claimed in claim 1, wherein perfluoroalkyl iodides of the formulae $F(CF_2)_i$—I, $(CF_3)_2CF$—$(CF)_j$—I, $F(CF_2)_k$—$CF(CF_3)$—I, $F(CF_2)_l$—$CF(CF_3)$—$CF_2$—I, $F(CF_2$—$CF(CF_3))_m$—I and $F(CF_2$—$CF_2)_n(CF_2$—$CF(CF_3))_p$—I, in which i, j, k, l, m, n and p are each, independently of one another, integers from 0 to 20, are used.

4. The process as claimed in claim 3, wherein use is made of perfluoroalkyl iodides of the formula $F(CF_2)_i$—I, where i is an integer from 2 to 16.

5. The process as claimed in claim 1, wherein the organic solvents used are alcohols.

6. The process as claimed in claim 5, wherein, during the preparation of the perfluorocarboxylic acids in alcoholic solvents, the corresponding perfluorocarboxylic esters form directly.

7. A process for the preparation of perfluorocarboxylic acids of the formula $R_F$—COOH, salts thereof and esters thereof from perfluoroalkyl iodides of the formula $R_F{'}$—I, in which $R_F$ and $R_F{'}$ are cyclic, branched or linear, saturated or unsaturated perfluoroalkyl radicals, consisting essentially of the steps:

activating the perfluoroalkyl iodides by exposure to light, in the presence of oxygen and in organic solvents having an OH functionality.

8. The process as claimed in claim 7, wherein perfluoroalkyl iodides of the formulae $F(CF_2)_i$—I, $(CF_3)_2CF$—$(CF)_j$—I, $F(CF_2)_k$—$CF(CF_3)$—I, $F(CF_2)_l$—$CF(CF_2$—I, $F(CF_2$—$CF(CF_3))_m$—I and $F(CF_2$—$CF_2)_n(CF_2$—$CF(CF_3))_p$—I, in which i, j, k, l, m, n and p are each, independently of one another, integers from 0 to 20, are used.

9. The process as claimed in claim 8, wherein use is made of perfluoroalkyl iodides of the formula $F(CF_2)_i$—I, where i is an integer from 2 to 16.

10. The process as claimed in claim 7, wherein the organic solvents used are alcohols, selected from the groups of lower branched, cyclic or linear alcohols having up to 10 carbon atoms.

11. The process as claimed in claim 10, wherein, during the preparation of the perfluorocarboxylic acids in alcoholic solvents, the corresponding perfluorocarboxylic esters form directly.

12. The process as claimed in claim 7, wherein the light source used can be UV light or daylight.

* * * * *